(12) United States Patent
Vastag et al.

(10) Patent No.: US 8,585,669 B2
(45) Date of Patent: Nov. 19, 2013

(54) ABSORBENT ARTICLE WITH ELASTIC SIDE PANELS

(75) Inventors: Eva Vastag, Härryda (SE); Karl Nyström, Göteborg (SE); Pernilla Lundahl, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 304 days.

(21) Appl. No.: 13/124,627

(22) PCT Filed: Oct. 16, 2008

(86) PCT No.: PCT/SE2008/051169
§ 371 (c)(1),
(2), (4) Date: Apr. 15, 2011

(87) PCT Pub. No.: WO2010/044715
PCT Pub. Date: Apr. 22, 2010

(65) Prior Publication Data
US 2011/0208149 A1    Aug. 25, 2011

(51) Int. Cl.
*A61F 13/15* (2006.01)

(52) U.S. Cl.
USPC ............ 604/385.24; 604/385.22; 604/385.26; 604/385.27; 604/387; 604/386; 604/385.01

(58) Field of Classification Search
USPC ............ 604/385.24, 385.22, 385.26, 385.27, 604/387, 396
See application file for complete search history.

(56) References Cited

U.S. PATENT DOCUMENTS

| | | |
|---|---|---|
| 4,662,875 A | 5/1987 | Hirotsu et al. |
| 5,133,707 A | 7/1992 | Rogers et al. |
| 5,226,992 A | 7/1993 | Morman |
| 5,897,546 A | 4/1999 | Kido et al. |
| 6,488,202 B1 | 12/2002 | Seitz et al. |
| 2004/0020579 A1 | 2/2004 | Durrance et al. |
| 2007/0049896 A1 | 3/2007 | Mills |

FOREIGN PATENT DOCUMENTS

| | | |
|---|---|---|
| EP | 0 646 062 | 8/1996 |
| EP | 0 756 855 | 2/1997 |
| EP | 1 035 818 | 4/2002 |
| RU | 2006121552 | 12/2007 |
| RU | 2328257 | 7/2008 |
| WO | 98/29251 | 7/1998 |
| WO | 01/21126 | 3/2001 |
| WO | 03/000165 | 1/2003 |
| WO | 03/034966 | 5/2003 |
| WO | 03/047488 | 6/2003 |
| WO | 2005/037159 | 4/2005 |
| WO | WO 2005/048900 A1 | 6/2005 |
| WO | 2006/007149 | 1/2006 |
| WO | 2006/036231 | 4/2006 |
| WO | 2006/071427 | 7/2006 |

*Primary Examiner* — Jacqueline F. Stephens
(74) *Attorney, Agent, or Firm* — Drinker Biddle & Reath LLP

(57) ABSTRACT

An absorbent article, in particular a diaper. The rear portion thereof includes a pair of elastic side panels attached to opposing longitudinal edges thereof. The front portion of the article includes at least two landing zones upon which the elastic side panels overlap when the article is fastened. An area of the front portion located at least around each landing zone includes a plurality of first indicia in a first pattern. Each of said elastic side panels also includes a plurality of second indicia in a second pattern. The distance between adjacent second indicia including the second pattern increases as the elastic side panel is stretched. When the elastic side panels are stretched by a predetermined force, the second pattern on the elastic side panels matches the first pattern around each landing zone.

14 Claims, 7 Drawing Sheets

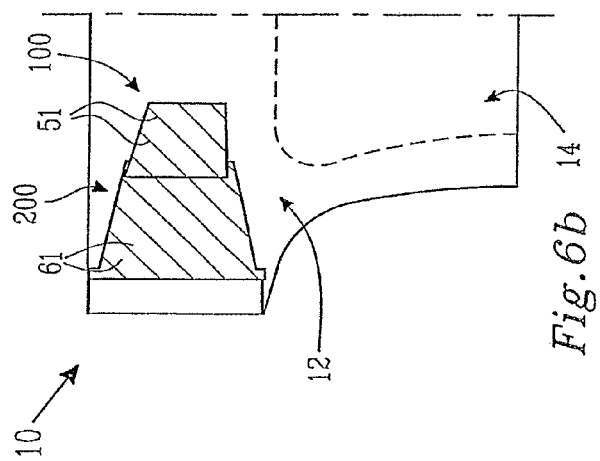
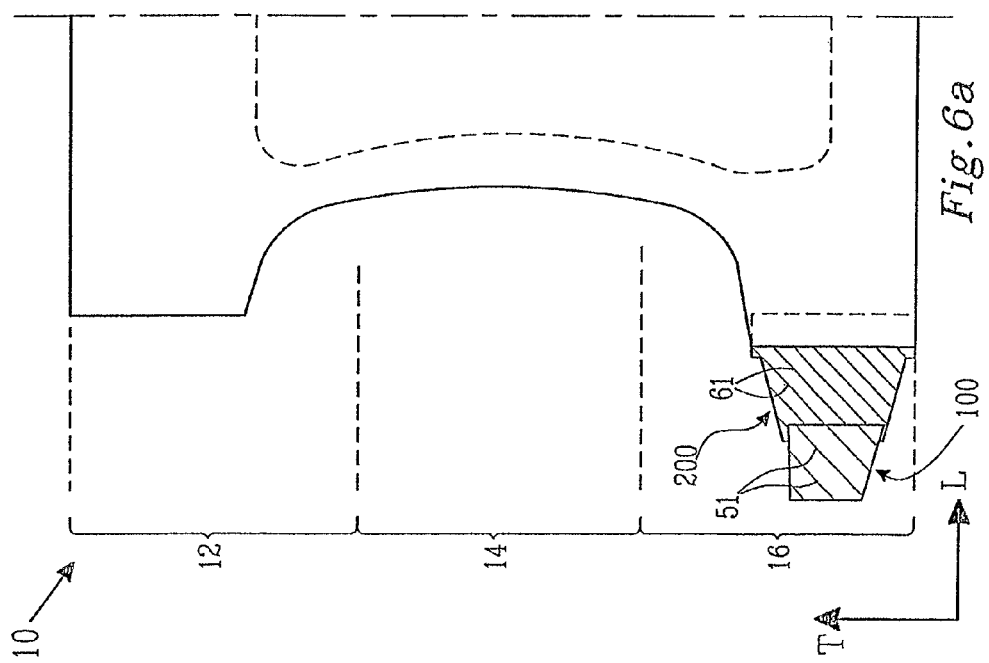

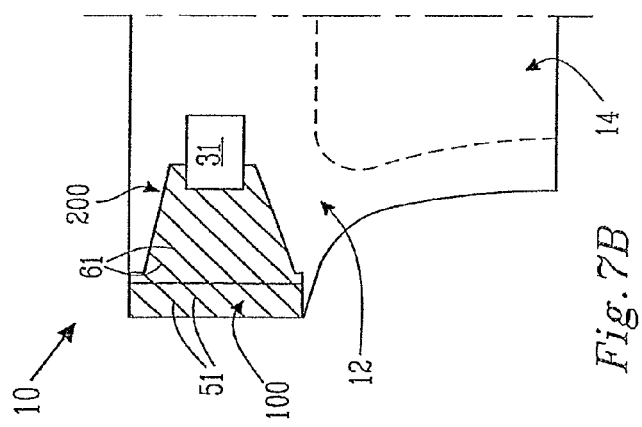
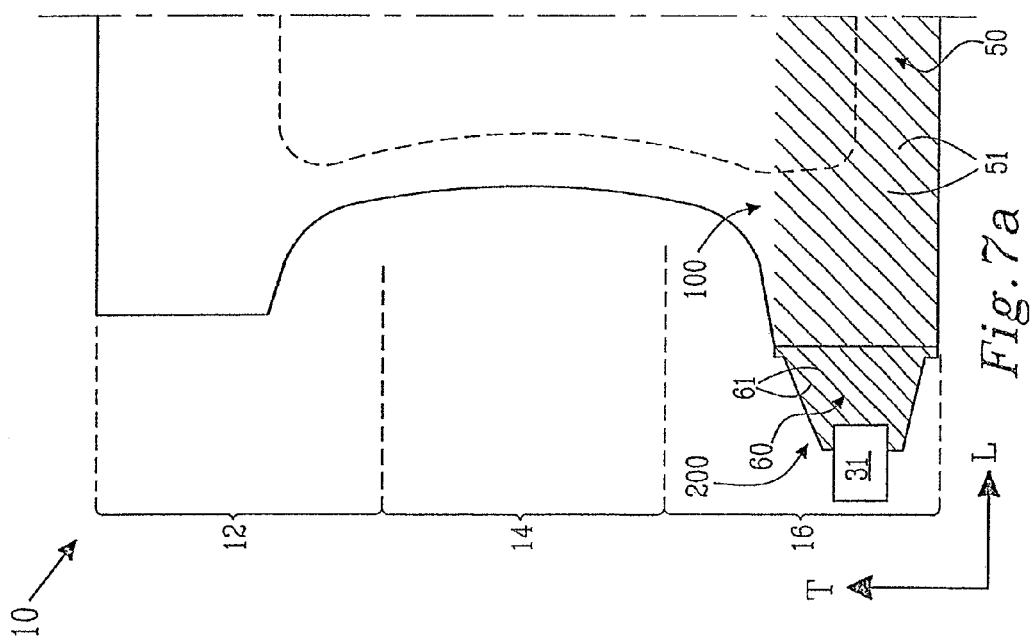

ABSORBENT ARTICLE WITH ELASTIC SIDE PANELS

CROSS-REFERENCE TO PRIOR APPLICATION

This application is a §371 National Stage Application of PCT International Application No. PCT/SE2008/051169 filed Oct. 16, 2008.

FIELD OF THE INVENTION

The present disclosure relates to an absorbent article, in particular a diaper, having elastic portions, particularly, elastic side panels. The diaper is designed so that a predetermined tension can be obtained in the elastic portions.

BACKGROUND

Disposable absorbent articles, such as diapers, are used to collect and store bodily exudates such as urine and feces from wearers, such as babies. To prevent undesired leakage, absorbent articles should fit well against the wearer, and a number of measures have been adopted to provide good fit.

One such measure is the use of elastic side panels in diapers. These are panels which extend laterally from, for example, the rear of the diaper, and include fastening elements at their distal ends which attach to the front of the diaper, thus securing the diaper about the waist of the wearer. However, due to their elastic nature, the amount of extension which the elastic side panels undergo can vary. An elastic side panel which is not sufficiently tight will risk that the diaper is not secure about the wearer, causing it to slip out of place or fall off completely. In addition, loose diapers are susceptible to leakage. On the other hand, an elastic side panel which is stretched too tightly about the wearer's waist may cause discomfort and pain to the wearer, and may also risk distorting the diaper, causing poor fit and leakage. It is particularly important to ensure that elastic side panels in baby diapers are extended by the correct amount (i.e. with the correct force), as elastic side panels allow a small diaper to be stretched above its optimal level to fit a larger baby, when a larger diaper size may in fact be more appropriate.

It is known to provide indicia on elastic side panels which change shape upon extension of the side panel. When the appropriate extension has been reached, the indicia have a certain appearance. For example, WO 05/037159 shows an example in which a drawing of a cartoon rabbit is compressed laterally before the elastic side panel is stretched, but which becomes more rounded when a suitable degree of extension has been reached. A disadvantage with this solution is that it is rather subjective. What one person applying the diaper might consider a suitable shape for the indicia, may be different to what another person thinks. As such, the extension in the elastic side panel in WO 05/037159 can vary, depending on the user's perception of what the "correct" form of the indicia should be. In addition, the solution provided by WO 05/037159 gives no indication as to the correct placement of the elastic side panel on the front of the diaper (e.g. in the longitudinal direction of the diaper).

Another solution is provided by WO 01/21126. A first indicium element is located on the outermost edge of a side panel, while a second indicium element is located in the front waist region of the diaper. Closing the diaper correctly results in the first and second indicium elements forming an image which is a combination of the first and second indicium elements. For instance, the first indicium element is shown as a balloon, while the second is a teddy bear. Fastening the diaper correctly provides a combined image of a teddy bear holding the balloon. However, this solution does not require that the indicium element on the side panel changes shape upon stretching, so the diaper user does not have the clear impression of a changing degree of stretch.

U.S. Pat. No. 5,133,707 concerns an adhesive fastening tape for a diaper, which is transparent yet embossed to create indicia. Once the tape is applied to the diaper, the indicia on the tape will disappear against the colored landing zone.

US 2007/0049896 discloses an absorbent article having a size fit indicating means for indicating when the article is too large for a wearer. Two target strips for fasteners are provided on the front body panel and a visual sizing indicator is positioned between the two target strips, so that when the fasteners overlap the sizing indicator, it is an indication that the article is too large.

U.S. Pat. No. 5,897,546 discloses a diaper having a fastening system including tape fasteners and a target area in the form of a transparent receiving sheet intermittently bonded to the outer sheet of the front body panel by means of an adhesive serving as a positioning indicator for the tape fasteners.

U.S. Pat. No. 6,488,202 discloses a device and method for identifying a size of an absorbent article which is appropriate for a potential wearer based on at least two characteristics, such as weight and height.

WO 03/034966 discloses an absorbent article having fasteners in the form of hook material engageable with the outer nonwoven surface of the front body panel and wherein landing zone graphics are printed in the target area for the fasteners and covered by an outer nonwoven and visible through the outer nonwoven.

Co-pending PCT application PCT/SE07/000637 discloses an absorbent article having size fit indicating means which is hidden when the correct diaper size is used, but revealed when the diaper is too small.

SUMMARY

The present disclosure, among other things, aims to address the problems associated with obtaining correct placement of an elastic portion of an absorbent article, e.g. a diaper. In particular, it provides an elastic portion in which accurate placement of an elastic side panel can be achieved in both the longitudinal and transverse directions, and in which it is clearly indicated when the correct force is present in the elastic portion. These aims can be achieved in a simple, economical manner, often without the requirement for additional printing or materials in the diaper.

In a first aspect, the present disclosure relates to an absorbent article that extends in the longitudinal (L) and transverse (T) directions, and includes a front portion, a rear portion and a crotch portion arranged between the front portion and the rear portion in the longitudinal direction. The absorbent article includes at least one elastic portion and at least one non-elastic portion.

The non-elastic portion includes a plurality of first indicia in a first pattern, while the elastic portion includes a plurality of second indicia in a second pattern. The distance between adjacent second indicia including the second pattern increases as the elastic portion is stretched, such that, when the elastic portion(s) are stretched by a predetermined force, the second pattern on the elastic portion(s) matches the first pattern in the non-elastic portion(s).

In one embodiment, the at least one elastic portion includes a pair of elastic side panels attached to opposing longitudinal edges of the rear portion, each of the elastic side panels including at least one fastening means; and wherein the at least one fastening means is adapted to fasten to the front portion, thus forming the absorbent article into a pant-shape.

Suitably, the non-elastic portion includes the at least one fastening means. Alternatively, the non-elastic portion may include the rear portion.

In a particular embodiment, the non-elastic portion includes the front portion and forms at least two landing zones upon which the elastic side panels overlap when the fastening means are fastened to the front portion; wherein an area of the front portion located at least around each landing zone includes a plurality of first indicia in a first pattern and each of the elastic side panels also includes a plurality of second indicia in a second pattern, wherein the distance between adjacent second indicia including the second pattern increases as the elastic side panel is stretched such that, when the elastic side panels are stretched by a predetermined force, the second pattern on the elastic side panels matches the first pattern around each landing zone.

Suitably, each landing zone has first and second edges extending in the transverse direction (T), and the first pattern of first indicia extends to the at least first and/or second edges, and each elastic side panel has corresponding first and second edges extending in the transverse direction (T) which are intended to overlie the first and second edges of the landing zones respectively, when the article is fastened. The second pattern of second indicia on the elastic side panels extends to at least one of the first and second edges, such that, when the elastic side panels are stretched by a predetermined force, the second pattern on the elastic side panels forms a continuation of the first pattern around each landing zone at the first and/or second edges.

At least one second indicia on the elastic side panels may extend to at least one of the first or second edges of the elastic side panel, and at least one first indicia on the landing zones may be arranged such that it forms a continuation of the at least one second indicia of the elastic side panels.

The first pattern on the non-elastic portion may include a repeating pattern of regularly-spaced first indicia. Similarly, the second pattern on the elastic portion may include a repeating pattern of regularly-spaced second indicia.

All first indicia including the first pattern may be identical, as may all second indicia including the second pattern. Additionally, the first indicia including the first pattern may be identical to the second indicia including the second pattern, and the first pattern may be identical to the second pattern when the elastic portion is stretched to the predetermined force. Suitably, the second pattern extends across substantially the entire elastic portion.

BRIEF DESCRIPTION OF THE DRAWINGS

Embodiments of the invention will now be described in more detail with reference to the enclosed schematic figures, in which:

FIG. 6A illustrates another embodiment of the present invention, in an unstretched state, in which the non-elastic portion of the diaper is the fastening means.

FIG. 6B illustrates the embodiment of FIG. 6A, in a stretched state.

FIG. 7A illustrates another embodiment of the present invention, in an unstretched state, in which the non-elastic portion of the diaper is the rear portion of the diaper.

FIG. 7B illustrates the embodiment of FIG. 7A, in a stretched state.

DETAILED DESCRIPTION OF PREFERRED EMBODIMENTS

Figure 1:
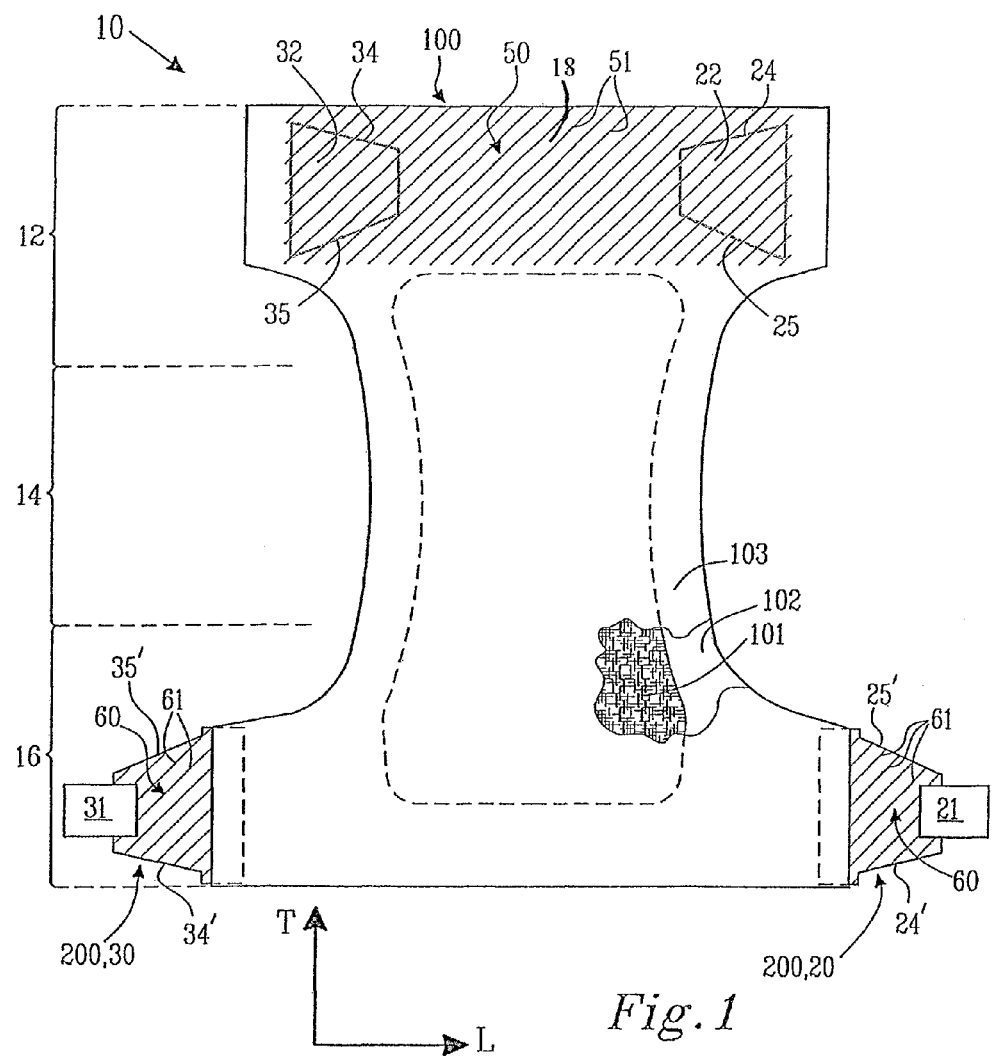
FIG. 1 shows a plan view of a diaper according to one embodiment of the invention seen from its garment facing side.

FIG. 1 shows an embodiment of an absorbent article 10 in the form of an open diaper (e.g. a baby diaper) or incontinence guard. The article 10 extends in the longitudinal (L) and transverse (T) directions, as shown. The article 10 includes a front portion 12, which in the embodiment shown in the drawings is the part of the article that in use is intended to extend over the stomach and front hip area of the wearer. The article 10 also includes a rear portion 16 which in the shown embodiment is the part of the pant diaper that in use is intended to extend over the back and the rear hip area of the wearer. The article 10 is symmetrical about the longitudinal center line.

A crotch portion 14 is arranged between the front portion 12 and the rear portion 16 in the longitudinal direction of the article 10. The crotch portion 14 of the article 10 is the part of the article that in use is intended to extend through the wearer's crotch area, between the legs. An absorbent core 101 is disposed in the crotch portion 14 and extends into the front and rear portions 12 and 16. The absorbent core 101 is typically disposed between an inner coversheet 102 and an outer coversheet 103.

The term "inner coversheet" refers to the liquid permeable material sheet forming the inner cover of the absorbent garment and which in use is placed in direct contact with the skin of the wearer. The inner coversheet can include a nonwoven material, for example spunbond, meltblown, carded, hydroentangled, wetlaid etc. Suitable nonwoven materials can be composed of natural fibers, such as wood pulp or cotton fibres, man-made fibres, such as polyester, polyethylene, polypropylene, viscose, rayon etc. or from a mixture of natural and man-made fibers. The inner coversheet material may further be composed of tow fibers, which may be bonded to each other in a bonding pattern, as, for example disclosed in EP-A-1 035 818. Further examples of inner coversheet materials are porous foams, apertured plastic films etc. The materials suited as inner coversheet materials should be soft and non-irritating to the skin and be readily penetrated by body fluid. The inner coversheet may further be different in different parts of the absorbent garment.

The "outer coversheet" refers to the material forming the outer cover of the absorbent garment. The outer coversheet may be the same or different in different parts of the absorbent garment. At least in the area of the absorbent core, the outer coversheet includes a liquid impervious material; a thin plastic film, including, for example, a polyethylene or polypropylene film; a nonwoven material coated with a liquid impervious material; a hydrophobic nonwoven material, which resists liquid penetration; or a laminate of a plastic film and a nonwoven material. The outer coversheet material may be breathable so as to allow vapor to escape from the absorbent core, while still preventing liquids from passing therethrough. Examples of breathable outer coversheet materials are porous polymeric films, nonwoven laminates of spunbond and meltblown layers, and laminates of porous polymeric films and nonwoven materials. In a particular embodiment, the outer coversheet includes a nonwoven material on at least the undergarment-facing surface thereof.

The "absorbent core" is the absorbent structure disposed between the two coversheets of the absorbent garment in at least the crotch region thereof. The absorbent core can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof In particular embodiments, the hydrogel polymers are lightly cross-linked to render the material substantially water insoluble. In further particular embodiments, the superabsorbent materials are further surface cross-linked so that the outer surface or shell of the superabsorbent particle, fiber, flake, sphere, etc. possesses a higher crosslink density than the inner portion of the superabsorbent. The superabsorbent materials may be in any form which is suitable for use in absorbent composites including particles, fibers, flakes, spheres, and the like.

A high liquid storage capacity is provided by the use of high amounts of superabsorbent material. For an absorbent core including a matrix of hydrophilic fibers, such as cellulosic fibers, and superabsorbent material, the proportion of superabsorbent material can be between 10 and 90% by weight, more preferably between 30 and 70% by weight.

Absorbent garments can have absorbent cores including layers of different properties with respect to liquid receiving capacity, liquid distribution capacity, and storage capacity. The thin absorbent bodies, which are common in for example baby diapers and incontinence guards, often include a compressed, mixed or layered structure of cellulosic fluff pulp and superabsorbent polymers. The size and absorbent capacity of the absorbent core may be varied to suit different uses, such as infants or adult incontinent persons.

The absorbent core may further include an acquisition distribution layer placed on top of the primary absorbent body, which is adapted to quickly receive and temporarily store discharged liquid before it is absorbed by the primary absorbent core. Such acquisition distribution layers are well known in the art and may be composed of porous fibrous wadding or foam materials.

The article may further contain elastic features, such as leg elastics, waist elastics, raised leakage barriers along the absorbent core etc., which are known in the art, but not shown in the drawings.

The absorbent article 10 includes at least one elastic portion 200 and at least one non-elastic portion 100.

The absorbent article 10 may include one, two or more elastic portions 200. The elastic portions 200 may include any suitable elastic material used in the construction of diapers 10. For example, the elastic portions 200 may include an elastic film, an elastic nonwoven, or laminates thereof. Films may be films of polyalkenes, such as polyethylene, polypropylene, polybutene etc, or polyesters. Nonwovens may be spunbonded, spunlaced (hydroentangled), meltblown, carded, airlaid or wetlaid nonwovens. Fibers of the nonwoven material may be natural fibers, such as wood pulp or cotton fibers, man-made fibers, such as polyester, polyethylene, polypropylene, viscose, rayon etc., or from a mixture of natural and man-made fibres. In particular embodiments, each elastic portion 200 is unitary; i.e. it includes the same material over substantially its entire surface area. The elastic portions 200 may have any suitable shape, such as rectangular, square, triangular, or trapezoid. In that the elastic portion is "elastic", it is meant that a force of 7N provides an extension of 15-50% in the elastic portion. A tensile test procedure suitable for use in the present invention can be found in co-pending application PCT/SE2007/050340.

The elastic portion 200 includes a plurality of second indicia 61 in a second pattern 60, wherein the distance between adjacent second indicia 61 including the second pattern 60 increases as the elastic portion 200 is stretched.

The elastic portion 200 may include an elastic component in the belt of a belt diaper. However, in one embodiment, the at least one elastic portion 200 includes a pair of elastic side panels 20, 30 attached to opposing longitudinal edges of the rear portion 16, as shown in FIGS. 1-4B. This embodiment will be discussed in more detail in the following.

The elastic side panels 20, 30 may be any suitable elastic material as described above for the elastic portion 200. In particular embodiments, each elastic side panel 20, 30 is unitary; i.e. it includes the same material over substantially its entire surface area. The elastic side panels 20, 30 may have any suitable shape, such as rectangular, square, triangular, or trapezoid. Typically, each elastic side panel 20, 30 has an extension in the longitudinal direction of between 50 and 110 mm, and an extension in the transverse direction of between 30 and 70 mm. The elastic side panels 20, 30 on each side of the article should be the same size and shape as each other, and include the same materials as each other.

The elastic side panels may be constituted by an elastic film. The elastic film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials.

The elastic side panels may be constituted by an elastic laminate including at least one elastic film layer and at least one non-woven layer, in which the layers have been ultrasonically bonded, adhesively bonded or extrusion bonded, or bonded using a combination of the bonding methods. In particular embodiments of the elastic laminates, the first and second layers of fibrous material are chosen so that they, in combination with the intermediate elastic film layer, provide a soft and cloth-like feel to the laminate. Examples of suitable materials are carded webs and spun-bonded materials. Examples of suitable polymers used in the fibrous materials are polyethylene, polyesters, polypropylene and other polyolefin homo-polymers and copolymers. Natural fibres, for example cotton, may also be used as long as they provide the required properties. A mixture of polymers can contribute to a higher flexibility of the non-woven layer.

The elastic side panels may include a stretch activated laminate, activated by hot stretching for example, and known in the art. The elastic laminate may be a laminate between two or more non-woven layers, two or more film layers, or a combination of film and non-woven layers. One group of elastic laminates are so called "stretch-bonded" laminates, in which the elastic layer is stretched in at least one direction before laminating it with one or more inelastic layers. After the tension is removed from the elastic layer it can freely retract to its un-tensioned state, and the inelastic layer(s) laminated thereto become gathered, giving a three-dimensional puckering. Alternatively, the second elastic region may include one or more elastic strips or threads contractably affixed between web materials, which may be inelastic.

Another group of elastic laminates are so called "neck bonded" laminates, which refer to laminates in which an elastic material is bonded to a non-elastic material while the non-elastic member is extended under conditions reducing its width or "necked". "Neck bonded laminate" refers to a composite material having at least two layers in which one layer is a necked, non-elastic layer and the other layer is an elastic layer. The layers are joined together when the non-elastic layer is in an extended condition.

A further group of elastic laminates are disclosed in for example WO 03/047488, in which inelastic non-woven layers are laminated to an elastic film layer, and the laminate is stretched above the point of failure of the non-woven materials, so that the inelastic layers break. Inelastic non-woven layers may also be laminated to an un-stretched elastic film layer. The elasticity of the laminate is then activated by mechanical stretching.

Examples of elastic laminates are described in EP-B-0 646 062, WO 98/29251, WO 03/000165 and U.S. Pat. No. 5,226, 992. Examples of commercially available elastic laminates are Fabriflex™ 306 from Tredegar and PK 6358 from Nordenia.

In that the side panels 20, 30 are "elastic", it is meant that a force of 7N provides an extension of 15-50% in the elastic portion. The elastic side panels 20, 30 are at least elastic in the transverse direction of the article 10, but may be elastic in other directions as well. Suitably, the elastic side panels 20, 30 are the most elastic components of the diaper 10, and in particular embodiments, the outer coversheet 103 of the article 10 is substantially inelastic.

Each of the elastic side panels 20, 30 includes at least one fastening means 21, 31, e.g. preferably one fastening means 21, 31 as shown in the Figures. The fastening means 21, 31 are substantially inelastic. The fastening means 21, 31 are adapted to fasten to the front portion 12 of the diaper 10, so that the article 10 will assume a pant-like shape. The fastening means 21, 31 illustrated in FIG. 1 are attached to each distal end of each elastic side panel 20, 30 and are intended to be fastened to the outside of the front portion 12. The fastening means 21, 31 may include an adhesive tape or a mechanical fastener, especially a hook fastener of a hook-and-loop fastening means. A "hook-and-loop fastener" refers to complementary fastening means having a "hook" portion and a "loop" portion and which are refastenable. The term "hook" as used herein refers to any element capable of engaging another element, the so called "loop" portion. The term "hook" is not limited to only "hooks" in its normal sense, but rather encompasses any form of engaging elements, whether unidirectional or bi-directional. The term "loop" is likewise not limited to "loops" in its normal sense, but also encompasses any structure capable of engaging with a "hook" fastener. Examples of "loop" materials are fibrous structures, like nonwoven materials. Hook-and-loop fasteners are for example available from Velcro, USA.

Further examples of mechanical fasteners are button and holes or button loops, snap fasteners and the like. Combinations of adhesive and mechanical fasteners may also be provided.

To allow fastening means 21, 31 to fasten to the front portion 12, at least a region of said front portion 12 may include at least one receiving portion 18. Receiving portion 18 is selected to be complementary to the fastening means 21, 31 on the elastic side panels 20, 30. Therefore, if the fastening means 21, 31 includes the hook portion of a hook-and-loop fastener, the receiving portion 18 may include a loop material, or even another hook material. If the fastening means 21, 31 includes an adhesive tape, the receiving portion 18 may include a material to which the adhesive tape can adhere. The receiving portion 18 may include separate material to that of the outer coversheet 103 in the front portion 12; alternatively, it may include a region, or the entirety of the outer coversheet 103, at least in the front portion 12. For instance, a nonwoven outer coversheet 103 provides a good receiving portion for a fastening means 21, 31 which is a hook material. A single receiving portion 18 may extend across the front portion 12 in the transverse direction. Alternatively, two or more receiving portions 18 may be located at the longitudinal edges of the front portion 12. The at least one receiving portion 18 is suitably located at a selected distance from the transverse edge of the front portion 12 in a transverse central area thereof, which means the area centred over the longitudinal central axis L1 of the article. The receiving portion(s) 18 may be indicated by colour, character, graphic, text or combinations thereof. The receiving portion 18 may partially or completely overlap or coincide with the landing zones 22, 32 and/or the first pattern 50.

Figure 2:
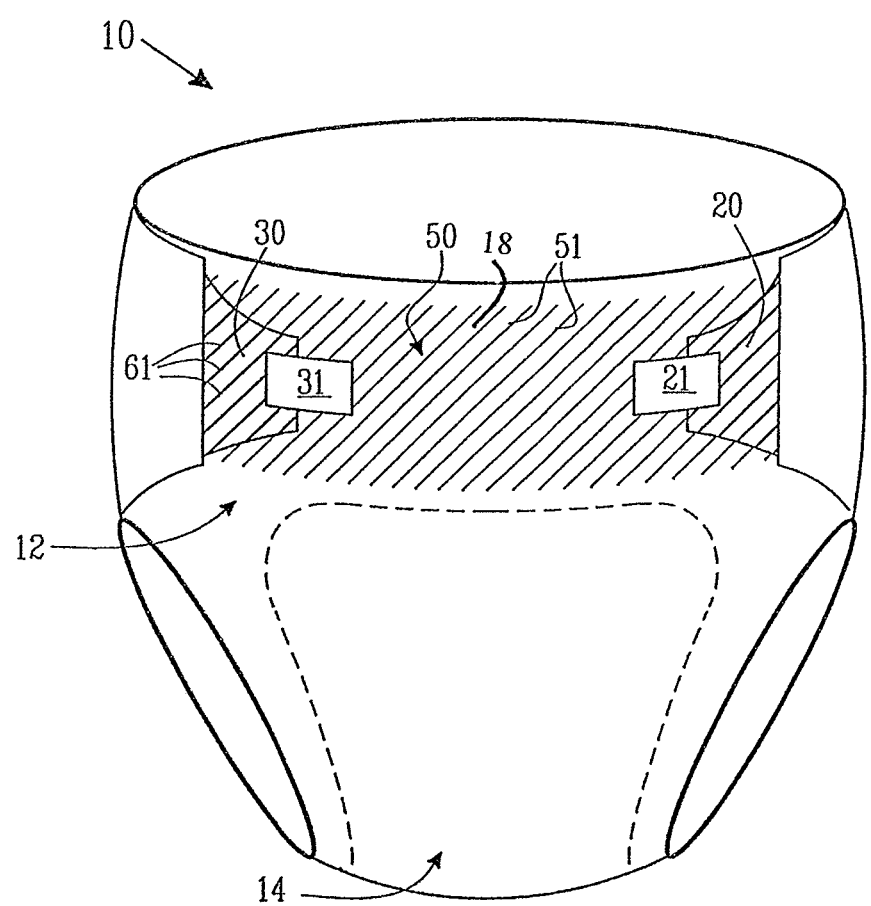
FIG. 2 illustrates the configuration of the diaper of FIG. 1 when in use with the fasteners applied in the target area.

The front portion 12 also includes at least two landing zones 22, 32, which are the areas on the front portion which are overlapped by the elastic side panels 20, 30 when the fastening means 21, 31 are fastened to said front portion 12 (when the elastic side panels 20, 30 are extended at the predetermined extension). This is illustrated in FIG. 2. The landing zones 22, 32 may overlap partially or completely with the receiving portions 18 on the front portion 12 of the diaper 10.

As an alternative to the above, the elastic side panels 20, 30 can be attached to opposing longitudinal edges of the front portion 12, while it is the rear portion 16 which comprises the at least two landing zones 22, 32. In this case, the diaper is worn in reverse, in that the front portion 12 overlaps the rear portion 16 at the longitudinal edges thereof. In this case, all references to "front" and "back" in this description should be reversed.

Each of the elastic portions 200 includes a plurality of second indicia 61 in a second pattern 60. In the embodiment of the Figures, each of the elastic side panels 20, 30 therefore includes a plurality of second indicia 61 in a second pattern 60. Suitably, all second indicia 61 including the second pattern 60 are identical. The second pattern 60 may extend across substantially the entire elastic portion 200 of the diaper 10, e.g. across substantially each entire elastic side panel 20, 30. Indicia 61 may include discrete printing or embossing on the elastic portions 200, or elastic side panels 20, 30, or combinations of printing and embossing. Suitable indicia 61 may include spots, lines, geometric shapes, e.g. circles, squares, rectangles, ovals, stars, triangles etc., drawings of everyday objects, such as cars, houses, trees, flowers, animals, faces etc, or drawings of baby-related objects e.g. pacifiers, diaper pins, teddy bears etc. Indicia may also be irregular in shape. Indicia may also take the form of words or lettering. By "plurality of indicia" is meant at least 2 indicia, preferably at least 3 indicia, more preferably at least 5 indicia, most preferably at least 10 indica. Suitably, all second indicia 61 are identical.

The absorbent article 10 may include one, two or more non-elastic portions 100. The non-elastic portions 100 are a region or component of the absorbent article 10 which are substantially inelastic; i.e. they do not extend elastically and return to their original form when stretched. The non-elastic portion 100 includes a plurality of first indicia 51 in a first pattern 50.

In a particular embodiment (FIGS. 1-4B), the non-elastic portion 100 is comprised by the front portion 12 and forms at least two landing zones 22, 32 upon which the elastic side panels 20, 30 overlap when the fastening means 21, 31 are fastened to said front portion 12.

In the embodiments of FIGS. 1-4B, the non-elastic portion 100 is comprised by the front portion 12. An area of the front portion 12 located at least around each landing zone 22, 32 includes a plurality of first indicia 51 in a first pattern 50. Suitably, all first indicia 51 including the first pattern 50 are identical. In that the first pattern 50 is located "around" the landing zone, is meant that the first pattern 50 extends along at least one edge of the landing zone 22, 32.

If desired, the first pattern 50 may not extend into the landing zones 22, 32. However, the first pattern 50 may be located within a portion of, or the entirety of the landing zones 22, 32. The first pattern 50 may extend between the two landing zones 22, 32, such that it extends across the front portion 12 of the diaper 10 in the transverse direction T. In fact, the first pattern 50 may extend across substantially the entire front portion 12 of the diaper 10, or even across substantially the entire outer coversheet 103 of the diaper. Suitable first indicia 51 may be formed in the same way as described above for the second indicia 61, and may include the same shapes. Suitably, all first indicia 51 including the first pattern 50 are identical.

In particular embodiments, the first and second indicia 51, 61 are identical, as are the first and second patterns 50, 60.

In that the indicia 51, 61 are arranged in a pattern 50, 60, it is meant that indicia on the elastic portion 200 or on the non-elastic portion 100 repeat in a regular, predictable way, in which indicia are a predetermined distance apart and/or have a predetermined location with respect to one another. The shortest straight edge-to-edge distance between adjacent indicia 51 in the non-elastic portion 100 is suitably between 1 and 20 mm, preferably between 5 and 10 mm. Suitably, the shortest straight edge-to-edge distance between adjacent indicia 61 in the elastic portions 200, in their stretched state is the same as that between adjacent indicia 15 in the non-elastic portion 100.

Figure 5A:
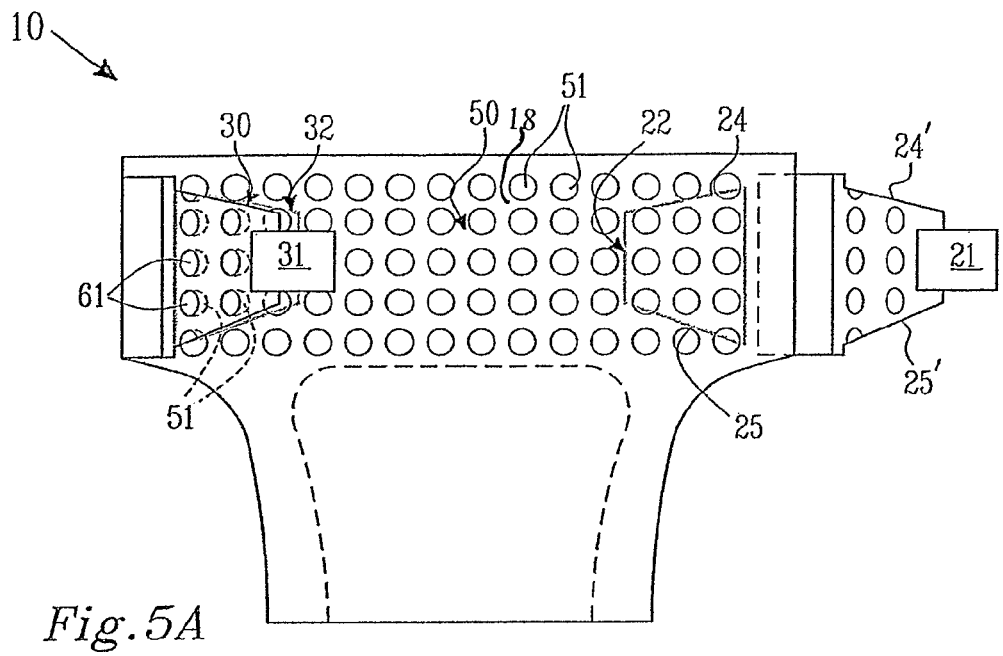
FIG. 5A illustrates another embodiment of the pattern of the elastic side panel in an unstretched state, overlapped on the pattern of the landing zone.
Figure 5B:
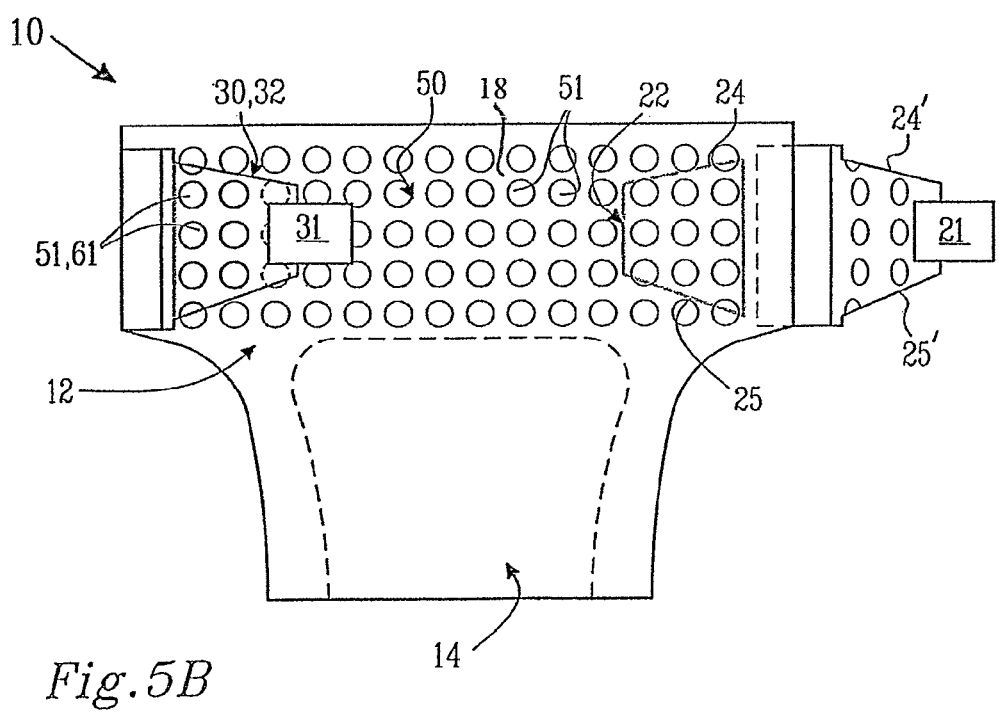
FIG. 5B illustrates another embodiment of the pattern of the elastic side panel in a correctly-stretched state, overlapped on the pattern of the landing zone.

Alternatively, or additionally, the non-elastic portion 100 may be comprised by the at least one fastening means 21, 31, as shown in FIGS. 5A and 5B.

In FIG. 5a, a first pattern 50 of first indicia 51 is located on the fastening means 21, 31. A second pattern 60 of second indicia 61 is located on the elastic side panels 20, 30. When the elastic side panels 20, 30 are stretched by a predetermined force, as shown in FIG. 5B, the second pattern 60 on the elastic side panels 20, 30 match the first pattern 50 on the fastening means 21, 31.

Alternatively, or additionally, the non-elastic portion 100 may include the rear portion 16, as shown in FIGS. 6A and 6B.

In FIG. 6A, a first pattern 50 of first indicia 51 is located on the rear portion 16. A second pattern 60 of second indicia 61 is located on the elastic side panels 20, 30. When the elastic side panels 20, 30 are stretched by a predetermined force, as shown in FIG. 6B, the second pattern 60 on the elastic side panels 20, 30 match the first pattern 50 on the rear portion 16.

As the elastic portions 200 (e.g. elastic side panels 20, 30) are elastic, stretching these portions 200 (e.g. elastic side panels 20, 30) causes the distance between adjacent second indicia 61 in the second pattern 60 to increase. When the diaper illustrated in FIG. 1 is placed on a user, the side panels 20, 30 are stretched in at least the transverse direction T until the required tension in the side panel is obtained.

When the elastic portion(s) 200 are stretched by a predetermined force, the second pattern 60 on the elastic portion(s) 200 matches the first pattern 50 in the non-elastic portion(s) 100. In the embodiment of FIGS. 1-4B, when the elastic side panels 20, 30 are stretched by a predetermined force, the second pattern 60 on the elastic side panels 20, 30 is such that it matches the first pattern 50 on the front portion 12.

The predetermined force is a value determined by the manufacturer of a diaper, at which the article does not sit too tightly on a wearer, nor too loosely. It is typically desirable that the elastic side panels 20, 30 provide a force of around 7N in the waist of a diaper. Such a force keeps the diaper in place, but is also not too tight about the wearer's waist.

Stretching the side panels 20, 30 causes the indicia 61 themselves to be enlarged, but also causes the inter-indicia spacing to increase. In that the second pattern 60 "matches" the first pattern 50, it is meant that either the size of the first indicia 51 is the same as the size of the second indicia 61 at the predetermined stretch, or that corresponding distances between adjacent indicia in each pattern 50, 60 is the same at the predetermined stretch.

Suitably, each landing zone 22, 32 has first 24, 34 and second edges 25, 35 extending in the transverse direction (T). The first pattern 50 of first indicia 51 around the landing zones 22, 32 extends to at least said first 24, 34 and/or said second 25, 35 edges. Each elastic side panel 20, 30 has corresponding first 24', 34' and second 25', 35' edges extending in the transverse direction (T) which are intended to overlie the first 24, 34 and second 25, 35 edges of the landing zones 22, 32 respectively, when the article 10 is fastened. The second pattern 60 of second indicia 61 on the elastic side panels 20, 30 extends to at least one of said first 24, 34 and second 25, 35 edges. When the elastic side panels 20, 30 are stretched by a predetermined force, the second pattern 60 on the elastic side panels 20, 30 forms a continuation of the first pattern 50 around each landing zone 22, 32 at said first 24, 34 and/or second 25, 35 edges.

Additionally, at least one second indicia 61 on the elastic side panels 20, 30 may extend to at least one of the first 24, 34 or second 25, 35 edges of the elastic side panel 20, 30. In combination with this, at least one first indicia 51 in the first pattern 50 on front portion 12 may be arranged such that it forms a continuation of the at least one second indicia 61 of the elastic side panels 20, 30.

In a particular embodiment, the first indicia 51 including the first pattern 50 are identical to the second indicia 61 including the second pattern 60, and the first pattern 50 is identical to the second pattern 60 when the elastic side panels 20, 30 are stretched by the predetermined force.

Figure 3A:
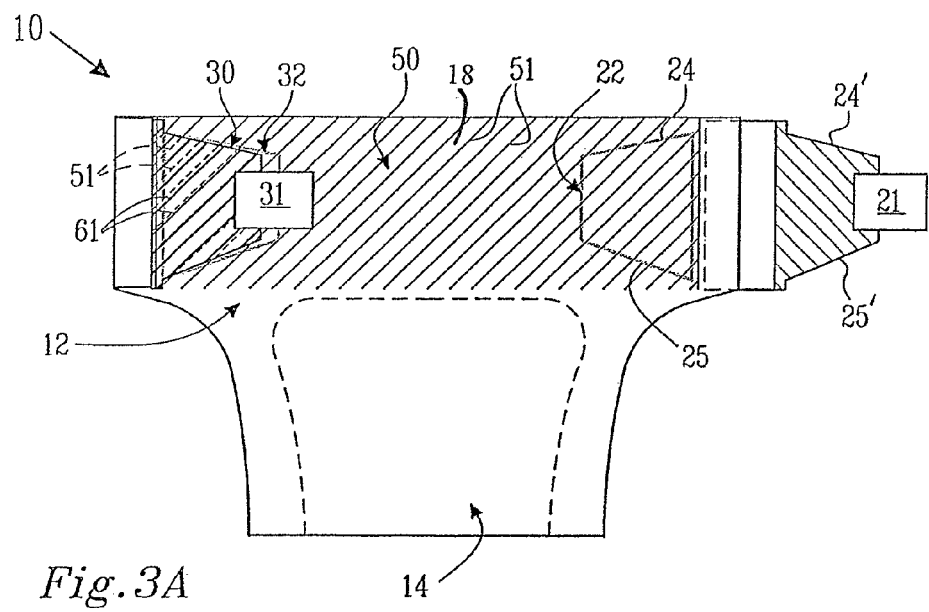
FIG. 3A illustrates one embodiment of the pattern of the elastic side panel in an unstretched state, overlapped on the pattern of the landing zone.
Figure 3B:
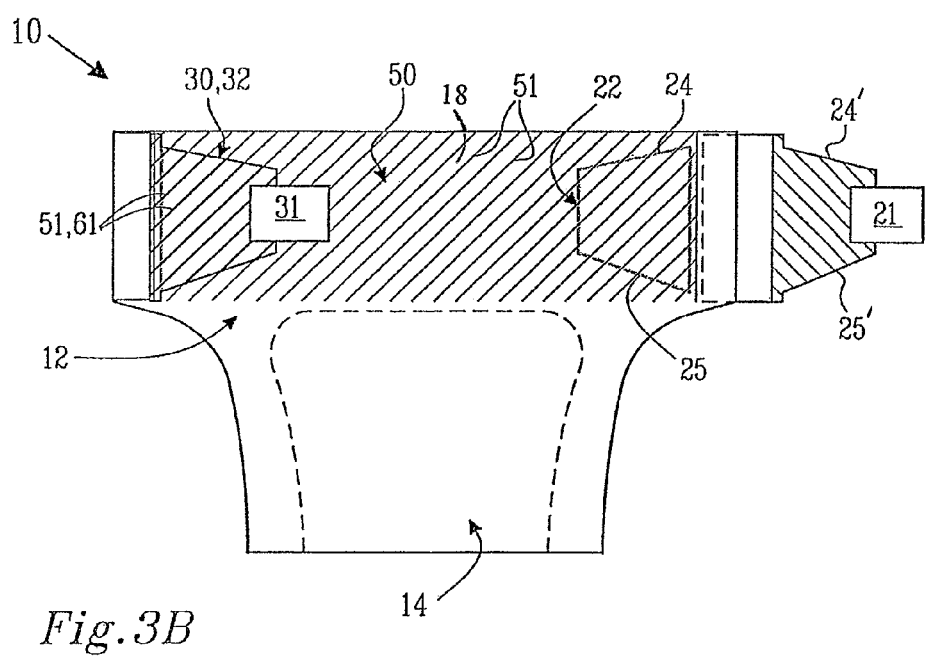
FIG. 3B illustrates one embodiment of the pattern of the elastic side panel in a correctly-stretched state, overlapped on the pattern of the landing zone.

An example is shown in FIG. 3A, in which the first pattern 50 includes indicia 51 in the form of straight parallel lines, with a given spacing. The second pattern 60 includes indicia 61 which are also in the form of straight parallel lines, aligned parallel to the indicia 51 of the first pattern 50, but with a smaller inter-indicia spacing when the side panel 20, 30 is not stretched. Stretching the side panel 20, 30 increases the inter-indicia spacing in the second pattern 60. When the predetermined stretch is obtained, the inter-indicia spacing in the second pattern 60 is the same as the inter-indicia spacing in the first pattern 50, as seen in FIG. 3B. The fastening means 21, 31 are then fastened to the receiving portion 18 to provide a diaper fastened at the correct tension. Using diagonal parallel lines, as per FIGS. 3A and 3B, allows the placement of the elastic side panels 20, 30 in both transverse and longitudinal directions to be specified.

Figure 4A:
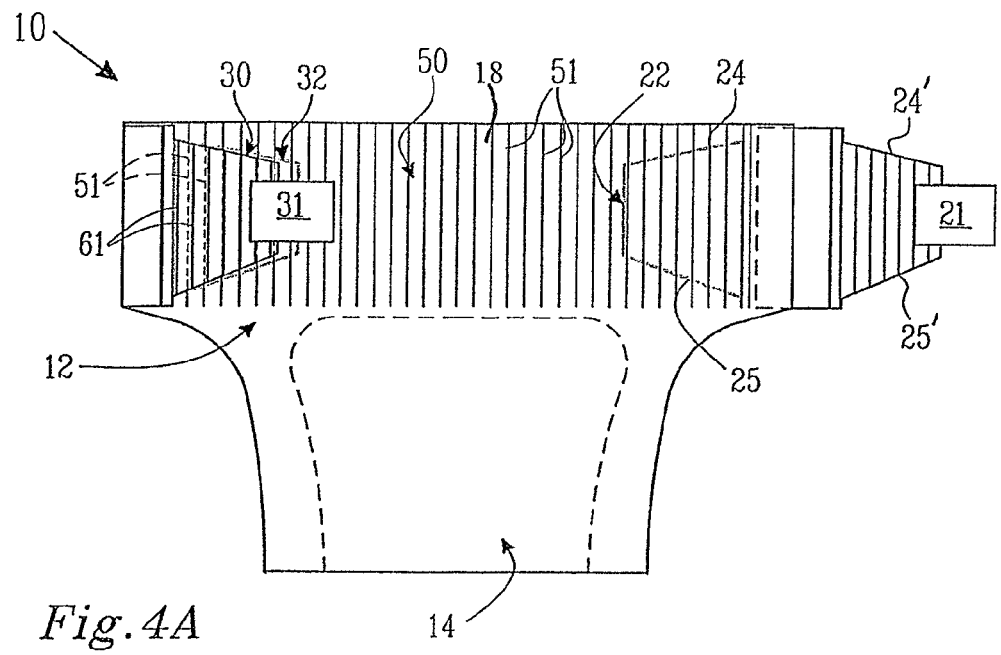
FIG. 4A illustrates another embodiment of the pattern of the elastic side panel in an unstretched state, overlapped on the pattern of the landing zone.
Figure 4B:
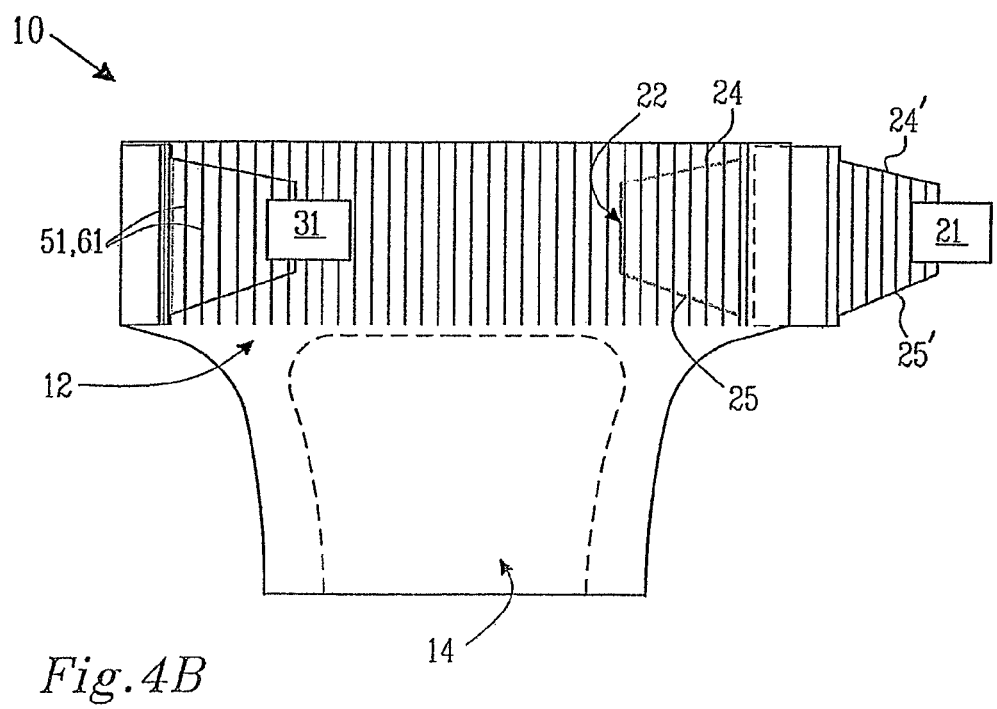
FIG. 4B illustrates another embodiment of the pattern of the elastic side panel in a correctly-stretched state, overlapped on the pattern of the landing zone.

The example shown in FIGS. 4A and 4B is similar to that of FIGS. 3A and 3B, except that the parallel lines are aligned in the longitudinal direction. This is a simpler embodiment to that of FIGS. 3A and 3B, as the positioning of the elastic side panels 20, 30 in the transverse direction need only be considered.

Another example is shown in FIG. 5A, in which the second pattern 60 includes first indicia 61 in the form of ovals, the major axes of which are aligned in the longitudinal direction of the article 10, and which have a first inter-indicia spacing in the transverse direction. The first pattern 50 includes first indicia 51 which are in the form of circles, with an inter-indicia spacing in the transverse direction which is bigger than that of the second pattern 60 when the side panel 20, 30 is not stretched. Stretching the side panel 20, 30 increases the inter-indicia spacing in the second pattern 60, and changes the oval-shaped indicia to circles. When the predetermined stretch is obtained, the inter-indicia spacing in the second pattern 60 is the same as the inter-indicia spacing in the first pattern 50, and both the second indicia 61 and the first indicia 51 are substantially circular, as seen in FIG. 5B. The fastening means 21, 31 are then fastened to the receiving portion 18, to provide a diaper fastened at the correct tension.

Suitable combinations of first and second indicia 51, 61 may be selected by the skilled person. Instead of being the same, the first and second indicia may be complementary. For example, the second indicia 61 may comprise spots, and the first indicia 51 may comprise circles, such that, when the elastic side panel 20, 30 is stretched overlapped on the landing zone 22, 32, the spots of the second indicia 61 are located within the circles of the first indicia 51.

The elastic portions 200, (e.g. the elastic side panels 20, 30) may be transparent, so that any first pattern 50 located in the landing zones 22, 32 can be seen through the side panels 20, 30 when the diaper is fastened. This means that the first and second indicia 51, 61 can be seen at the same time. However, the elastic portions 200 may also be non-transparent, i.e. opaque.

Either the first 50 or the second 60 pattern may be incorporated into the overall design of the diaper 10, so that matching of the two patterns by the user is almost subconscious.

By adjusting the dimensions of the second pattern 60 (e.g. the inter-indicia spacing), various predetermined stretches in the side panels 20, 30 can be obtained. During manufacture of the diaper 10, the same patterning apparatus can be used to provide the first and second patterns 50, 60; the second pattern 60 can be applied to the material of the elastic side panels 20, 30 while the panels are extended by the predetermined force. This helps to ensure that, when the article 10 is assembled, the first and second patterns 50, 60 match as closely as possible.

Although the invention has been described in relation to an open diaper, the invention is equally applicable to a belt diaper. In this case, the elastic portion 200 may include a section of the belt of the diaper, while the non-elastic portion 100 may include a different section of the belt of the diaper.

The invention has been described with reference to a number of embodiments and examples. However, the invention should not be considered as limited by these embodiments. Instead, the skilled person can vary the materials, components and arrangement of the absorbent article within the scope of the claims.

The invention claimed is:

1. An absorbent article extending in the longitudinal and transverse directions comprising a front portion, a rear portion, and a crotch portion arranged between said front portion and said rear portion in the longitudinal direction,
   wherein the absorbent article comprises at least one elastic portion and at least one non-elastic portion,
   wherein said at least one non-elastic portion comprises a plurality of first indicia in a first pattern and the at least one elastic portion comprises a plurality of second indicia in a second pattern, and
   wherein the distance between adjacent second indicia comprising the second pattern increases as the at least one elastic portion is stretched such that, when the at least one elastic portion is stretched by a predetermined force, the second pattern on the at least one elastic portion matches the first pattern on the at least one non-elastic portion.

2. The absorbent article according to claim 1, wherein the at least one elastic portion comprises a pair of elastic side panels attached to opposing longitudinal edges of the rear portion, each of said elastic side panels comprising at least one fastening element to fasten to the front portion to form the absorbent article into a pant-shape.

3. The absorbent article according to claim 1, wherein the at least one non-elastic portion comprises at least one fastening element to fasten to the rear portion to form the absorbent article into a pant shape.

4. The absorbent article according to claim 1, wherein the at least one non-elastic portion comprises said rear portion.

5. The absorbent article according to claim 2, wherein the at least one non-elastic portion comprises said front portion and forms at least two landing zones upon which the elastic side panels overlap when the at least one fastening element is fastened to said front portion,
   wherein an area of the front portion located at least around each landing zone comprises a plurality of first indicia in a first pattern and each of said elastic side panels also comprises a plurality of second indicia in a second pattern, and
   wherein the distance between adjacent second indicia comprising the second pattern increases as the elastic side panel is stretched such that, when the elastic side panels are stretched by a predetermined force, the second pattern on the elastic side panels matches the first pattern around each landing zone.

6. The absorbent article according to claim 5, wherein each landing zone has first and second edges extending in the transverse direction, and the first pattern of first indicia extends to at least one of said first edges and said second edges, and each elastic side panel has corresponding first and second edges extending in the transverse direction which are intended to overlie the first and second edges of the landing zones respectively, when the article is fastened, and wherein said second pattern of second indicia on the elastic side panels extends to at least one of said first edges and said second edges such that, when the elastic side panels are stretched by a predetermined force, the second pattern on the elastic side panels forms a continuation of the first pattern around each landing zone at least at one of said first edges and said second edges.

7. The absorbent article according to claim 6, wherein at least one second indicia on the elastic side panels extends to at least one of the first edges and said second edges of the elastic side panels, and at least one first indicia on the landing zones is arranged such that it forms a continuation of said at least one second indicia of the elastic side panels.

8. The absorbent article according to claim 1, wherein the first pattern on the at least one non-elastic portion comprises a repeating pattern of regularly-spaced first indicia.

9. The absorbent article according to claim 1, wherein the second pattern on the at least one elastic portion comprises a repeating pattern of regularly-spaced second indicia.

10. The absorbent article according to claim 1, wherein all first indicia comprising the first pattern are identical.

11. The absorbent article according to claim 1, wherein all second indicia comprising the second pattern are identical.

12. The absorbent article according to claim 1, wherein the first indicia comprising the first pattern are identical to the second indicia comprising the second pattern, and the first pattern is identical to the second pattern when the at least one elastic portion is stretched to said predetermined force.

13. The absorbent article according to claim 1, wherein the second pattern extends across substantially all of the at least one elastic portion.

14. The absorbent article according to claim 1, wherein the distance between adjacent second indicia of the second pattern is smaller than the distance between adjacent first indicia of the first pattern when the predetermined force is not applied to the at least one elastic portion.

* * * * *